United States Patent [19]

Brasfiel

[11] 4,449,911

[45] May 22, 1984

[54] LATEX GLOVE METHOD AND APPARATUS FOR MAKING THE SAME

[75] Inventor: Bernard M. Brasfiel, Arlington, Tex.

[73] Assignee: Surgikos, Inc., Arlington, Tex.

[21] Appl. No.: 314,830

[22] Filed: Oct. 26, 1981

Related U.S. Application Data

[62] Division of Ser. No. 129,543, Mar. 12, 1980, Pat. No. 4,371,987.

[51] Int. Cl.³ .............................................. B29H 3/04
[52] U.S. Cl. .................................. 425/374; 425/274; 425/394
[58] Field of Search ................ 425/374, 328, 274, 394

[56] References Cited

U.S. PATENT DOCUMENTS

| | | | |
|---|---|---|---|
| 2,067,641 | 1/1937 | Millen | 425/274 |
| 3,304,576 | 2/1967 | Keesling et al. | 425/274 |
| 3,570,053 | 3/1971 | Rodrigues et al. | 425/274 |
| 3,694,117 | 9/1972 | Gould | 425/274 |

FOREIGN PATENT DOCUMENTS 469609  5/1975  U.S.S.R. ............................ 425/374

*Primary Examiner*—James H. Derrington
*Attorney, Agent, or Firm*—Michael Q. Tatlow

[57] ABSTRACT

An elastomeric surgical glove with an improved ring rolled cuff and a method and apparatus to produce the cuff is disclosed. The ring rolled cuff comprises alternating tightly rolled segments with loosely rolled segments. The ring rolled cuff is made by contacting the uncured glove on the glove form with a plurality of rotating wheels while the wheels are moved on the form from the wrist end of the form toward the hand end of the form. The portions of the cuff in contact with the wheels are tightly rolled, and the remaining portions are loosely rolled.

4 Claims, 10 Drawing Figures

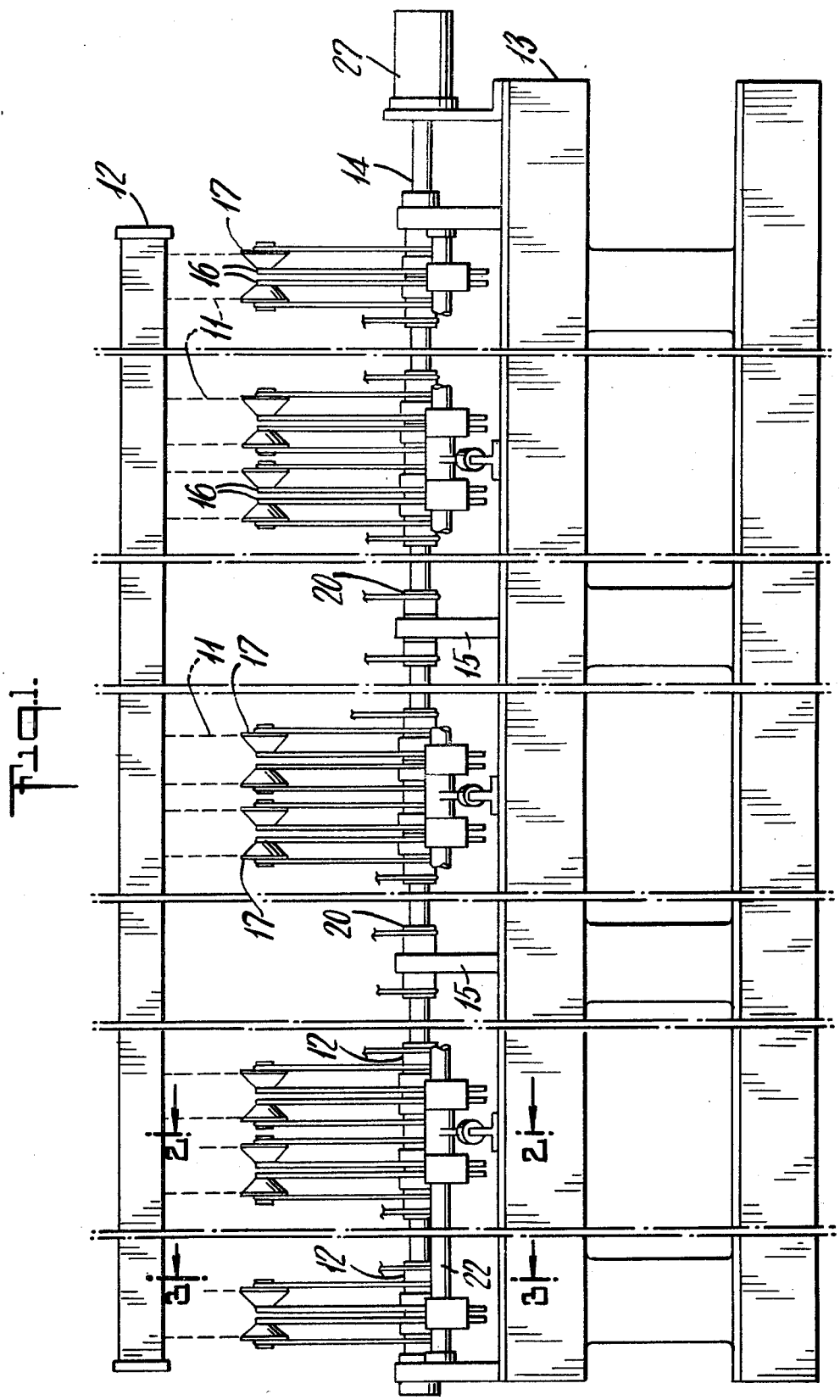

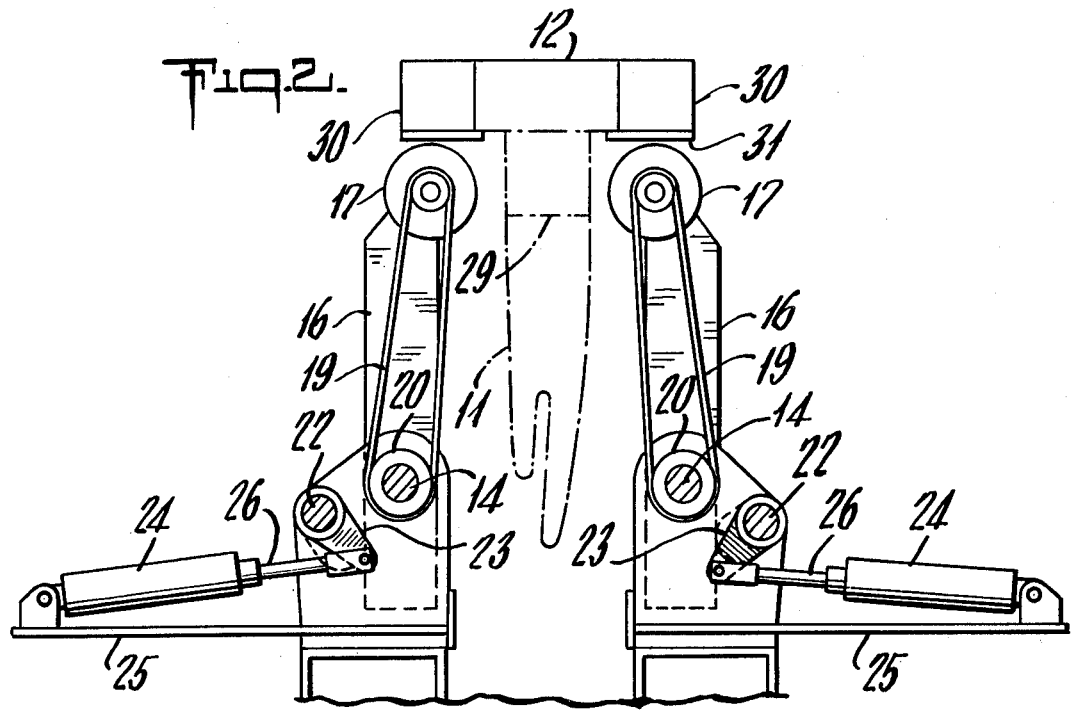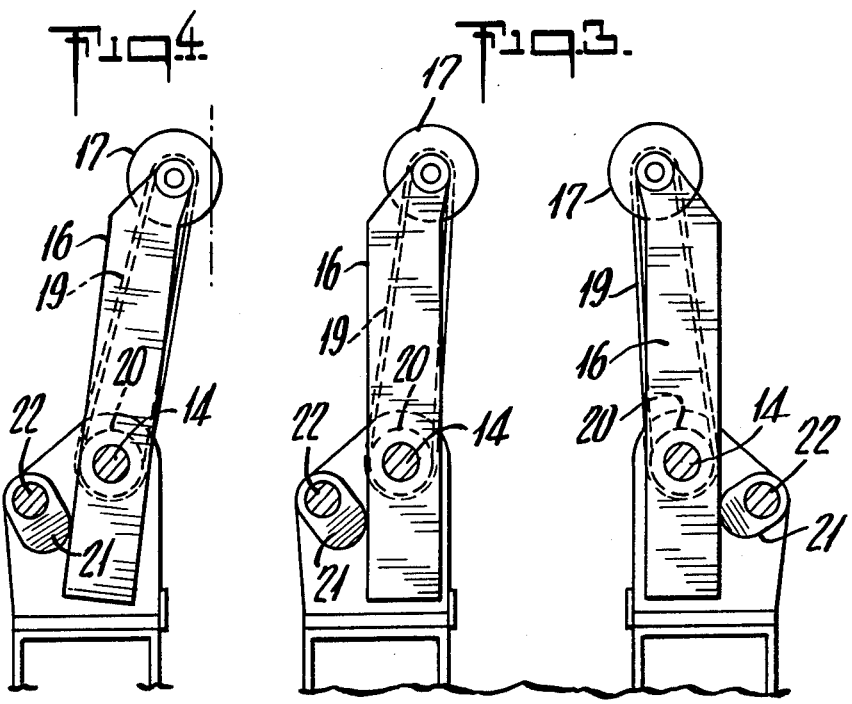

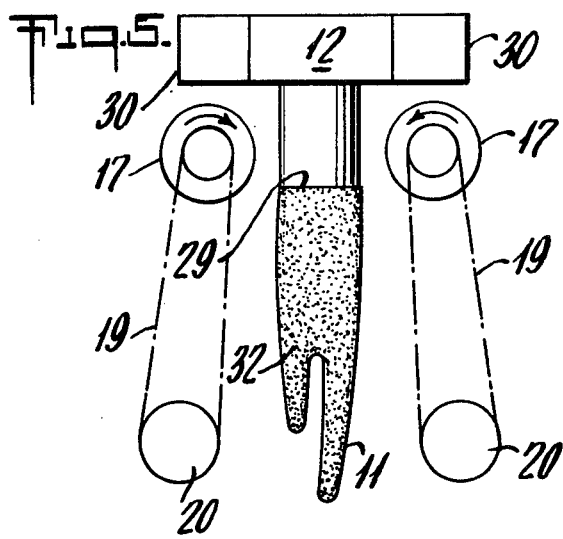
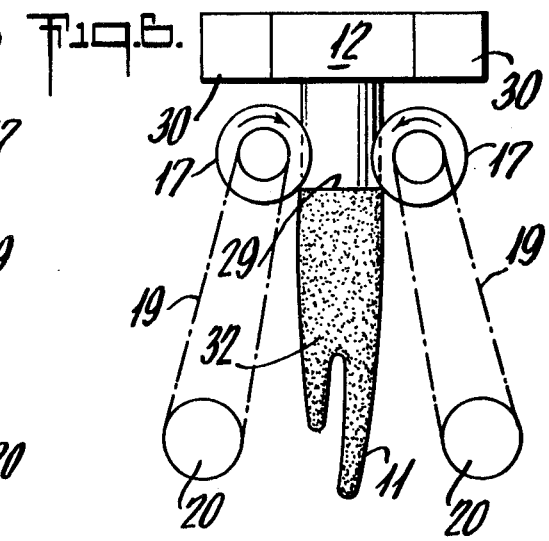
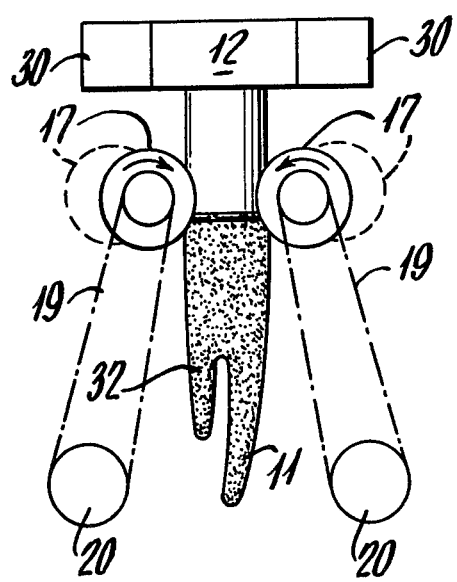
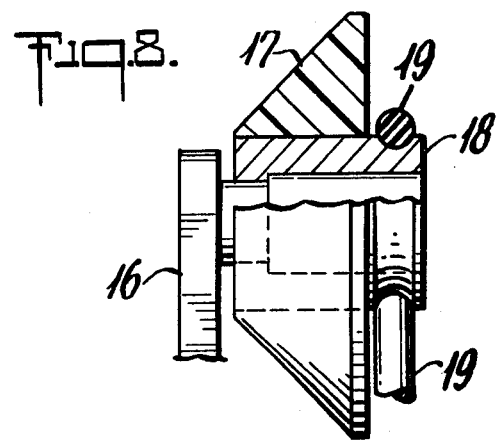
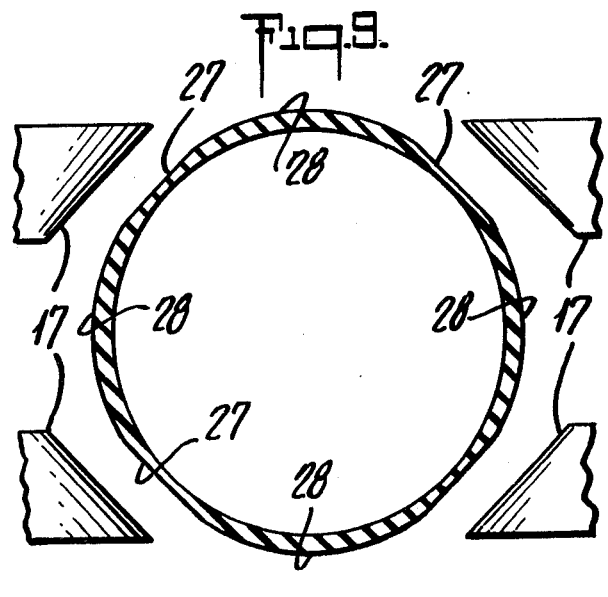
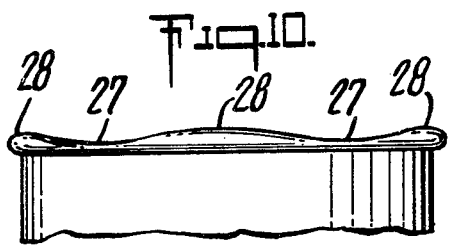

LATEX GLOVE METHOD AND APPARATUS FOR MAKING THE SAME

This application is a division of application No. 129,543 filed Mar. 12, 1980 now U.S. Pat. No. 4,371,987.

BACKGROUND OF THE INVENTION

Surgical or medical gloves are manufactured by dipping hand-shaped glove forms into a liquid bath containing an elastomeric material such as a rubber latex or a vinyl plastisol. The forms are withdrawn from the bath, and a coating or film of the elastomeric material is retained on the form. The elastomeric material is allowed to cure, usually with the application of heat, and the gloves are subsequently stripped from the forms for packaging and distribution.

The glove forms are made in the shape of a hand and are mounted on racks. The racks containing the forms are conveyed through various stations to apply the elastomeric material to the form to wash the coated forms to remove undesirable ingredients from the elastomer on the forms and to an oven where the elastomer is cured.

Some surgical or medical gloves are manufactured with a rolled cuff or circumferential bead around the cuff to aid in donning the glove and in preventing the glove from rolling down the wrist when in use. Other surgical and medical gloves are manufactured with a patterned wrist or cuff which inhibits cuff roll-down, which has been recognized as a problem with beaded cuffs. The pattern of the wrist portion of such gloves is usually made by providing the desired pattern on the glove forms used in making the gloves. The forms employed to make the patterned cuff are considerably more expensive than a smooth glove form. The patterned gloves are also difficult to strip from the form because of adhesion of the glove film to the form in the interstices in the pattern on the form. Patterned gloves of this type are disclosed in U.S. Pat. Nos. 2,821,718 and 4,095,293. The previously available ring rolling mechanisms were complex mechanisms which moved around the glove form in making the ring rolled cuff, or in which the glove form was rotated around the ring rolling mechanism. U.S. Pat. No. 2,482,418 discloses a ring rolling mechanism of the latter type. Because of the relative motion of the ring rolling mechanism and the forms, the individual glove forms were separated from each other on the rack by a considerable distance to allow the ring rolling mechanism to move around the form.

The separation of the forms on the rack to allow for the ring rolling mechanism reduced the number of glove forms that could be mounted on a rack. Since the glove making process is essentially a batch process, the overall production rate of the process is limited by the number of glove forms that can be mounted on a rack.

SUMMARY OF THE INVENTION

The present invention provides an improved apparatus of forming a ring rolled cuff on a surgical or medical glove. The present application allows glove forms to be mounted closer together on a rack, which results in greater production rates from a glove making production line. The present invention provides a ring rolling apparatus having multiple rollers or wheels each of which contacts a limited area on the free wrist end portion of the elastomeric film on the glove form and rolls that portion onto itself to form a number of densely rolled segments in the bead on the cuff end of the glove. The continuity of the elastomeric film allows those portions of the film of the cuff end of the glove, which is not in contact with the rollers, to be gathered into loosely rolled segments in the bead. The resulting glove has a rolled ring or bead which is composed of a number of individual tightly or densely rolled segments separated by a number of individual loosely rolled segments. The glove formed in this manner has a greater resistance to roll down in use than a glove with a uniformly rolled bead.

BRIEF DESCRIPTION OF THE DRAWINGS

FIG. 1 is a simplified side view of the present apparatus showing the ring rolling apparatus and the relative location of the glove forms in phantom.

FIG. 2 is a view taken along lines 2—2 of FIG. 1, again showing the glove form in phantom.

FIG. 3 is a view taken along lines 3—3 of FIG. 1 showing the location of the camming mechanism to move the ring rollers to a ready position.

FIG. 4 is a view of one of the ring rollers moving on its support arm to its operative position.

FIGS. 5–7 are schematic views showing the operating positions of the ring rollers in relation to the glove forms.

FIG. 8 is a detailed view, partly in section, of one of the ring rollers.

FIG. 9 is a top view of the ring roll formed on the glove with the relative position of the rollers shown in phantom.

FIG. 10 is a side view of the ring roll on the glove.

DETAILED DESCRIPTION OF THE INVENTION

The present invention is employed in a standard glove manufacturing process. The process that will hereinafter be described is that process employed in the manufacture of gloves from natural or synthetic rubber latex. It will be understood by those skilled in the art that if a different film forming elastomer is employed, certain of the process steps may be modified or eliminated entirely.

A number of glove forms are fixed to a rack which carries the forms through the various steps or stages of the process. The individual glove forms have the configuration of a hand and are made of aluminum, porcelain or other suitable material. The glove forms are either right or left handed. The rack is transferred from the various stations or stages in the process by a conveyor.

The glove forms may be coated with a release agent to allow for the easy removal of the completely finished glove. The forms are then dipped or sprayed with a coagulant for the rubber latex. The forms are then dipped into a tank of the latex with the finger portion of the forms pointed down, and the latex coagulates on the form. The forms are removed from the tank producing an uncured latex film on the form. The forms may be dipped into the same latex tank or into other latex tanks to build up the desired thickness of latex film on the form. The rack carrying the forms is then dipped into a washing solution which removes undesirable ingredients from the latex film. The forms are then conveyed to a station where the ring roll or bead is produced on the wrist portion of the form. The forms are then conveyed to an oven where the latex is cured by the application of heat. The completed gloves are then stripped from the forms and reversed so that the latex film in contact with the form becomes the outer surface of the finished glove. The glove may also be stamped with a symbol to indicate the size of the glove and may be dusted with a lubricating powder to aid in donning the glove.

Referring to the drawings, a number of individual glove forms 11 are shown supported on a rack 12. The rack 12 is supported in the proper position in relation to the ring rolling mechanism by rails 31 attached to an upper frame 30. Individual glove forms are attached to the rack by a suitable fastener. The ring rolling mechanism is supported on a base 13. The base 13 and the rack 12 are mounted so that they may be moved in a vertical direction relative to each other. This is most easily accomplished by mounting the base 13 on a support so that the base 13 and the ring rolling mechanism can be moved downwardly while the rack 12 remains in a fixed position.

The following description refers to the one side of FIG. 1. It is to be understood that the apparatus of the other side of FIG. 1 is a mirror image of the side shown.

There is a drive shaft 14 mounted in bearing blocks 15 which in turn are mounted on the base 13. The shaft is rotated by a drive means 27. Attached to the shaft 14, through free-turning bearings, are a series of roller arms 16. Each of the arms 16 is independently mounted on the shaft 14 through the free turning bearings. The independent mounting of the arms allows each arm to move the required distance to allow the surface of each wheel to achieve maximum surface contact with a particular form even if the particular form is misaligned on the rack. At the upper end of each roller arm 16 a roller 17 is attached through a free-turning bearing. The roller is in the shape of a truncated cone with a drive ring 18 below the base of the cone. A drive belt 19 is affixed around the drive ring 18 and a drive sheave 20 which is keyed onto shaft 14. The drive belt 19 may be a circular belt, as shown in the drawings, or may be a V-belt or a tooth rubber belt. The rotation of the shaft 14 will turn the rollers 17 through the drive belt 19.

Each individual roller 17 is made of a polyurethane polymer which provide a surface which will engage the latex film to produce the ring roll. The polyurethane wheel must have adequate hardness for durability in use but be sufficiently soft to grip the latex film. A Shore A Durometer hardness of about 55 is preferred. The face of the roller which contacts the form should be cut to present the maximum surface area to the form. When using four rollers per form, as shown in the drawings, the face of the roller is cut at an angle of 45 degrees. Although it is possible to use more or less than four rollers, it has been found that four rollers give good controllability of the ring rolling process while allowing for the maximum number of forms on a rack.

There are a series of cams 21 mounted on a fixed shaft 22. There is one cam 21 for each pair of roller arms 16 on each side of the unit. The cams 21 can be moved through a cam shaft actuator arm 23 by the action of cam actuating cylinder 24 which is mounted on the base 13 with an appropriate bracket 25. The cam actuating cylinder may be powered by air or hydraulic fluid. The purpose of the cam system is to move the roller arms 16 away from the glove forms 11 after the ring rolling operation has been completed. This is accomplished by the piston 26 of the cam actuating cylinder pushing the cam 21 against the roller arm 16. This causes the lower portion of the roller arm to rotate around the shaft 14 and move the upper portion of the roller arm carrying the roller 17 away from the form 11.

The operation of the ring rolling apparatus will best be understood with particular reference to FIGS. 5-7.

The rack 12 contains a number of glove forms 11 aligned in a row. The forms have previously been dipped in latex, and the latex-bearing forms have been washed to remove undesirable ingredients before the rack 12 reaches the ring rolling station. Each form is covered with an uncured latex film 32 in the shape of the form. When the rack reaches the ring rolling station, it actuates a switch, not shown, which starts the ring rolling process. The position of the rack 12, relative to the ring rolling device, is shown in FIG. 2 at the start of the process. The process starts with the rotation of the shaft 14 which turns the drive sheaves 20 which are keyed into the shaft 14. The drive belts 19 on the drive sheaves transmit power to the rollers 17 in the direction of the arrows. The cam 21 has been removed from contact with the arms 16, thus, allowing the arms 16 to freely pivot about the shaft 14. The rotation of the rollers 17 in the direction of the arrows causes the roller arms 16 to rotate around shaft 14 and bring the rollers 17 into contact with the form 11, as shown in FIG. 6. The rollers 17 first contact the forms 11 at a point on the forms which is above the latex dip level shown at 29 in FIG. 5. At the same time, the base 13 begins to move downwardly to move the rollers 17 down the form from the latex dip level 29 toward the fingers of the glove, as shown in FIG. 7. When the rollers have moved down the form the required distance to produce the ring roll, the cam actuating cylinders 24 are activated by appropriate switches to move the cam actuator arms 23 and the cams 21 into contact with the lower portion of the arms 16. The cams 21 move the lower portion of the arms 16 toward the center line of the apparatus causing the upper portion of the arms to rotate around the shaft and carry the rollers 17 away from the form 11.

The rollers 17 form the ring roll on the glove by rolling the latex film on the form onto itself. As the free edge of the glove at the dip line 29 is rolled, the relative vertical movement of the glove form 11 and the rollers 17 causes the ring first formed to enlarge as more of the film is rolled. The size of the ring roll can be controlled by adjusting the total vertical movement of the form.

The ring roll or bead formed on the cuff of the glove has the configuration shown in FIGS. 9 and 10 of the drawings. In that portion of the ring roll that has been directly contacted by the rollers 17, the ring is tightly rolled as shown at 27. The portions of the ring roll between the tightly rolled portions are comparatively loosely rolled as shown at 28. FIG. 9 shows the relative position of the rollers 17 in relation to the tightly or densely rolled segments 27 and the loosely rolled segments of the ring rolled cuff.

When the glove is worn by a surgeon, there is a noticeable reduced tendency for the glove to roll down the surgeon's wrist. It is believed that the pillow-like loosely rolled portions 28 of the ring roll create a greater surface area in contact with the cuff on the surgeon's gown. It appears that more force is required to roll down the cuff of the glove, much as an underinflated automobile tire requires more force to roll than a properly inflated tire.

I claim:

1. Apparatus to form a ring rolled bead on the cuff of an elastomeric glove applied to the surface of a glove form comprising:
   a rack containing a plurality of glove forms,
   a pair of drive shafts located on opposite sides of the rack containing said glove forms,
   a series of arms independently mounted on each of the shafts through free turning bearings,
   a wheel located on the free end of each of the arms,
   means to rotate the wheels,
   means to move the free ends of arms toward and away from the forms, and
   means to move the forms relative to the center of rotation of the wheels so that the wheels first contact the wrist portion of the glove form and move toward the hand portion of the glove form.

2. The apparatus of claim 1,
   wherein each series of arms is divided into pairs,
   a pair of said arms being located on each side of the glove forms,
   a cam positioned adjacent the free turning bearing of each of said arms and being movable to contact said arms and rotate the arms about said free turning bearings to move the wheel end of the arm in a direction away from said forms.

3. An apparatus to form a ring rolled bead on the cuff of an elastomeric glove applied to the surface of a glove form having a wrist portion and a hand portion comprising:
   a rack containing a plurality of glove forms, a pair of drive shafts spaced apart from each other on opposite sides of a support frame,
   a series of arms independently mounted on each of the shafts through free turning bearings,
   means to move said rack containing said glove forms between the opposite sides of said support frame to position individual glove forms adjacent the arms,
   a wheel at the free end of each of said arms,
   means to rotate the wheels,
   means to move the wheels into contact with the glove forms,
   means to move the support frame relative to said rack to move said wheels in a direction from the wrist portion of said glove forms toward the hand portion of said glove forms,
   means to move the wheels out of contact with said glove forms after the support frame has moved relative to the rack a predetermined distance.

4. The apparatus of claim 3 in which the face of each of said wheels contacting the glove forms is at an angle of 45°.

* * * * *